United States Patent
Lai et al.

(10) Patent No.: US 7,829,062 B2
(45) Date of Patent: Nov. 9, 2010

(54) METHOD OF PREPARING A MOLECULAR SIEVE COMPOSITION

(75) Inventors: Wenyih Frank Lai, Bridgewater, NJ (US); Robert Ellis Kay, Easton, PA (US)

(73) Assignee: ExxonMobil Chemical Patent Inc., Houston, TX (US)

( * ) Notice: Subject to any disclaimer, the term of this patent is extended or adjusted under 35 U.S.C. 154(b) by 734 days.

(21) Appl. No.: 11/698,500

(22) Filed: Jan. 26, 2007

(65) Prior Publication Data

US 2007/0191658 A1   Aug. 16, 2007

Related U.S. Application Data

(60) Provisional application No. 60/773,010, filed on Feb. 14, 2006.

(51) Int. Cl.
C01B 39/02   (2006.01)
(52) U.S. Cl. .................. 423/700; 423/702; 423/706
(58) Field of Classification Search .................. 423/700, 423/702, 706
See application file for complete search history.

(56) References Cited

U.S. PATENT DOCUMENTS

| | | | |
|---|---|---|---|
| 4,100,262 | A | 7/1978 | Pelrine et al. |
| 4,439,409 | A | 3/1984 | Puppe et al. |
| 4,826,667 | A | 5/1989 | Zones et al. |
| 4,873,067 | A | 10/1989 | Valyocsik et al. |
| 4,954,325 | A | 9/1990 | Rubin et al. |
| 4,973,781 | A | 11/1990 | Valyocsik et al. |
| 5,236,575 | A | 8/1993 | Bennett et al. |
| 5,250,277 | A | 10/1993 | Kresge et al. |
| 5,362,697 | A | 11/1994 | Fung et al. |
| 5,558,851 | A | 9/1996 | Miller |
| 5,871,650 | A | 2/1999 | Lai et al. |
| 5,895,769 | A | 4/1999 | Lai |
| 6,077,498 | A | 6/2000 | Diaz Cabanas et al. |
| 6,099,820 | A | 8/2000 | Miller |
| 6,936,744 | B1 | 8/2005 | Cheng et al. |
| 2005/0013774 | A1 | 1/2005 | Dakka et al. |

FOREIGN PATENT DOCUMENTS

| | | |
|---|---|---|
| CN | 1 296 913 | 5/2001 |
| EP | 0 174 121 | 3/1986 |
| EP | 0 284 206 | 9/1988 |
| EP | 0 293 032 | 11/1988 |
| EP | 0 999 182 | 5/2000 |
| EP | 1 105 348 | 6/2001 |
| EP | 1 249 428 | 10/2002 |
| EP | 1 061 046 | 9/2007 |
| WO | 92/12928 | 8/1992 |
| WO | 97/17290 | 5/1997 |
| WO | 03/006160 | 1/2003 |
| WO | WO 03/006405 | 1/2003 |
| WO | 03/029144 | 4/2003 |
| WO | 03/093230 | 11/2003 |
| WO | 2005/118476 | 12/2005 |
| WO | 2007/094949 | 8/2007 |

OTHER PUBLICATIONS

Inagaki et al., "Textural and Catalytic Properties of MCM-22 Zeolite Crystallized by the Vapor-Phase Transport Method", Bull. Chem. Soc. Jpn., 77, (2004), pp. 1249-1254.
Xu et al., "A Novel Method for the Preparation of Zeolite ZSM-5", J. Chem. Soc., Chem. Commun., (1990), pp. 755-756.
Matsukata et al., "Synthesis of zeolites under vapor atmosphere, Effect of synthetic conditions on zeolite structure", Microporous Materials, 1 (1993) pp. 219-222.
Kim et al., "Synthesis of zeolites by water-organic vapor-phase transport", Microporous Materials, 1 (1993), pp. 191-200.
Corma et al., "Synthesis and characterization of the MCM-22 zeolite", Zeolite 15: pp. 2-8, 1995.
Guray et al., "Synthesis of zeolite MCM-22 under rotating and static conditions", Microporous and Mesoporous Materials 31 (1999), pp. 241-251.
Lok et al., "The Role of Organic Molecules in Molecular Sieve Synthesis" Zeolites, vol. 3, Oct. 1983, pp. 282-291.
Marques et al., "Static crystallization of zeolites MCM-22 and MCM-49", Microporous and Mesoporous Materials 32 (1999), pp. 131-145.
Ravishankar et al., "Characterization and catalytic properties of zeolite MCM 22", Microporous Materials 4 (1995), pp. 83-93.
Baerlocher et al., Atlas of Zeolite Framework Types, Fifth Edition, 2001. (3 title pgs).

*Primary Examiner*—David M Brunsman
(74) *Attorney, Agent, or Firm*—Darryl M. Tyus

(57) ABSTRACT

A method of preparing a crystalline molecular sieve is provided, which method comprises
(a) providing a reaction mixture comprising at least one source of ions of tetravalent element Y, at least one source of alkali metal hydroxide, water, optionally at least one seed crystal, and optionally at least one source of ions of trivalent element X, said reaction mixture having the following mole composition:

| | |
|---|---|
| $Y:X_2 =$ | 10 to infinity |
| $OH^-:Y =$ | 0.001 to 2 |
| $M^+:Y =$ | 0.001 to 2 | wherein M is an alkali metal and the amount of water is at least sufficient to permit extrusion of said reaction mixture;
(b) extruding said reaction mixture to form a pre-formed extrudate; and
(c) crystallizing said pre-formed extrudate under vapor phase conditions in a reactor to form said crystalline molecular sieve whereby excess alkali metal hydroxide is removed from the pre-formed extrudate during crystallization. The crystalline molecular sieve product is useful as catalyst in hydrocarbon conversion processes.

24 Claims, 1 Drawing Sheet

METHOD OF PREPARING A MOLECULAR SIEVE COMPOSITION

CROSS REFERENCE TO RELATED APPLICATION

This application claims priority to U.S. Provisional Patent Application No. 60/773,010, filed Feb. 14, 2006, the disclosures of which are incorporated herein by reference in its entirety.

FIELD OF THE INVENTION

The present invention relates to a method of preparing a molecular sieve, particularly but not exclusively to a method for synthesizing a crystalline molecular sieve composition and a catalyst.

BACKGROUND

Molecular sieve materials, both natural and synthetic, have catalytic properties for various types of hydrocarbon conversion. Certain molecular sieves (e.g., zeolites, AlPOs, and/or mesoporous materials) are ordered, porous crystalline materials having a definite crystalline structure. Within the crystalline molecular sieve material there are a large number of cavities which may be interconnected by a number of channels or pores. These cavities and pores are uniform in size within a specific molecular sieve material. Since the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as a rigid three-dimensional framework of $SiO_4$ and Group IIIA element oxide (e.g., $AlO_4$) (as defined in the Periodic Table, IUPAC 1997). The tetrahedra are cross-linked by the sharing of oxygen atoms whereby the ratio of the total Group IIIA element (e.g., aluminum) and silicon atoms to oxygen atoms is 1:2. The electrovalence of the tetrahedra containing the Group IIIA element (e.g., aluminum) is balanced by the inclusion in the crystal of a cation, for example a proton, an alkali metal or an alkaline earth metal cation. This can be expressed as the ratio of the Group IIIA element (e.g., aluminum) to the number of various cations, such as $H^+$, $Ca^{2+}/2$, $Sr^{2+}/2$, $Na^+$, $K^+$, or $Li^+$, being equal to unity.

Molecular sieves that find application in catalysis include any of the naturally occurring or synthetic crystalline molecular sieves. Examples of these sieves include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is herein incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, "MCM-22 family material", silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

The term "MCM-22 family material" (or "material of the MCM-22 family" or "molecular sieve of the MCM-22 family"), as used herein, includes one or more of:

(i) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize said molecular sieve are obtained by standard techniques using the K-alpha doublet of copper as the incident radiation and a diffractometer equipped with a scintillation counter and associated computer as the collection system. Materials belonging to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of the aforesaid patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of said molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstrom (Å).

The MCM-22 family molecular sieves including MCM-22, MCM-49, and MCM-56 have various applications in hydrocarbon conversion processes. Unfortunately, industrial applications of zeolite catalysts have been hindered due to some major disadvantages associated with the current synthesis techniques that make large scale production of these catalysts complicated and therefore expensive. At present, crystalline zeolite catalysts are synthesized mainly by conventional liquid-phase hydrothermal treatment, including in-situ crystallization and seeding method, and the vapor phase transport method.

In the hydrothermal method, a reaction mixture of silica, alumina, caustic agent, an organic template or structure directing agent, and water is heated at a high temperature in a liquid phase to produce crystalline zeolite crystals (see also U.S. Pat. No. 5,871,650, Lai et al.). The main drawbacks of this method are the difficulty in assuring the uniformity of the crystallization conditions and limited reproducibility of high quality membranes.

In the vapor phase transport method, an extrudate reaction mixture of silica, alumina, caustic agent, an organic template or structure directing agent and water is heated at autogenous pressure at 100° C. in a sealed reactor for a number of days. The extrudate is then dried in a vacuum oven overnight and calcined in air at a high temperature for a further eight hours to produce a crystalline zeolite (see also U.S. Pat. No. 5,558,851, Sep. 24, 1996, Miller). This method is unsuitable for producing crystalline zeolite on a large scale as the process is complicated and it takes a long time. In addition, the resulting crystalline zeolite has a low crush strength and lacks uniformity and consequently has poor quality.

The present invention aims to obviate or at least mitigate the above described problems and/or to provide improvements generally.

SUMMARY OF THE INVENTION

According to an embodiment of the invention, there is provided a method and a catalyst as defined in any of the accompanying claims.

In an embodiment of the invention there is provided a method of preparing a crystalline molecular sieve comprising:

(a) providing a reaction mixture comprising at least one source of ions of tetravalent element Y, at least one source of alkali metal hydroxide, water, optionally at least one seed crystal, and optionally at least one source of ions of trivalent element X, said reaction mixture having the following mole composition:

| | |
|---|---|
| $Y:X_2 =$ | 10 to infinity |
| $OH^-:Y =$ | 0.001 to 2 |
| $M^+:Y =$ | 0.001 to 2 | wherein Y is a tetravalent element, X is a trivalent element, M is an alkali metal and the amount of water is at least sufficient to permit extrusion of said reaction mixture;

(b) extruding said reaction mixture to form a pre-formed extrudate; and (c) crystallizing said pre-formed extrudate under vapor phase conditions in a reactor to form said crystalline molecular sieve whereby excess alkali metal hydroxide is removed from the pre-formed extrudate during crystallization.

In this way, a more efficient and simpler vapor phase crystallization process is provided which no longer requires a binder for binding the crystallized zeolite prior to extrusion. The element Y ion source in the reaction mixture, eg silica where Y is silicon, acts as a binder to bind the reaction components after extrusion and prior to crystallization so that the pre-formed extrudate retains its structure during crystallization.

During the process, the level of alkali metal hydroxide required for the reaction is present at all times during crystallization as superfluous alkali metal hydroxide is removed. In this way the critical level of alkali metal hydroxide is maintained uniformly in the pre-formed extrudate mixture. The removal of excess alkali metal hydroxide results in the formation of a good quality sieve in-situ extrudate which has a uniform crystalline structure. In addition, the process allows more efficient utilization of the template or structure directing agent and element Y ion source eg silica. This makes it possible to eliminate the steps of decanting and filtration which are otherwise necessary in the production of molecular sieves on the basis of the afore described conventional methods.

Furthermore, since the reaction mixture is extruded prior to crystallization the crystalline sieve structure/morphology is not damaged in any way by a part-crystallization extrusion step which would otherwise affect its mechanical properties. This is a problem in sieves produced in conventional processes.

The sources of the various elements required in the final product may be any of those in commercial use or described in the literature, as may the method of preparation of the synthesis mixture.

In the present synthesis method, the source of ions of tetravalent element Y may be provided by a source of the oxide of the tetravalent element, $YO_2$. The source of the oxide preferably comprises solid $YO_2$, more preferably about 30 wt. % solid $YO_2$ in order to obtain the crystal product of this invention. When $YO_2$ is silica, the use of a silica source containing preferably about 30 wt. % solid silica, e.g., silica sold by Degussa under the trade names Aerosil or Ultrasil (a precipitated, spray dried silica containing about 90 wt. % silica), an aqueous colloidal suspension of silica, for example one sold by Grace Davison under the trade name Ludox, or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micro) favors crystal formation from the above mixture. Preferably, therefore, the $YO_2$, e.g., silica, source contains about 30 wt. % solid $YO_2$, e.g., silica, and more preferably about 40 wt. % solid $YO_2$, e.g., silica. The source of silicon may also be a silicate, e.g., an alkali metal silicate, or a tetraalkyl orthosilicate. Alternative tetravalent elements may be germanium, titanium and tin. The reaction mixture may contain a source of ions of a single tetravalent element such as silicon or of two or more tetravalent elements, eg silicon and germanium.

The source of the ions of the trivalent element X, when present, is preferably the oxide, $X_2O_3$. For example the trivalent element may be aluminum, and the ion (oxide) source is preferably aluminum sulphate or hydrated alumina. Other aluminum sources include, for example, other water-soluble aluminum salts, sodium aluminate, or an alkoxide, e.g., aluminum isopropoxide, or aluminum metal, e.g., in the form of chips.

The alkali metal of the hydroxide is advantageously potassium or sodium, the sodium source advantageously being sodium hydroxide or sodium aluminate. The alkali metal hydroxide may also comprise a caustic agent, preferably sodium hydroxide.

In a preferred embodiment of the method of the invention, the crystallization is carried out in the presence of a structure directing agent R. Thus in one embodiment, the reaction mixture additionally comprises R, such that the pre-formed extrudate comprises a structure directing agent R. In another embodiment, the structure directing agent R is made available to the crystallization reaction by being contained in the reactor but not in the pre-formed extrudate. In yet another embodiment the structure directing agent may form part of the reaction mixture used to form the pre-formed extrudate, and a further amount of structure directing agent R, may be provided in the reactor separate from the preformed extrudate.

Directing agent R is preferably selected from the group consisting of cycloalkylamine, azacycloalkane, diazacycloalkane, and mixtures thereof, with alkyl preferably comprising from 5 to 8 carbon atoms. Non-limiting examples of R include cyclopentylamine, cyclohexylamine, cycloheptylamine, hexamethyleneimine (HMI), heptamethyleneimine, homopiperazine, and combinations thereof.

The amount of the directing agent affects the cost and the product quality of the synthesis of a crystalline molecular sieve. The directing agent is generally the most expensive reactant(s) in the hydrothermal reaction mixture of many crystalline molecular sieves. The lower the amount of the directing agent in the hydrothermal reaction mixture, the cheaper the final molecular sieve produced. The term "low directing agent" as used herein means the molar ratio of the directing agent over the tetravalent element in the hydrothermal reaction mixture is less than 0.5, preferably less than 0.34, even more preferably less than 0.2, and most preferably less than 0.15.

In one embodiment of this invention $R:SiO_2$ molar ratio ranges from 0.001 to 0.34, preferably from 0.001 to 0.3, more preferably from 0.001 to 0.25, even more preferably from 0.001 to 0.2, and most preferably from 0.1 to 0.15.

The composition of the preformed extrudates and reaction parameters are critical for producing a high quality and a homogeneous phase product. In preferred embodiments, the $Y:X_2$ ratio may be 50 to 5000 and/or the $H_2O:Y$ ratio may be 0.5 to 5 and/or the $OH^-:Y$ ratio may be 0.1 to 1 and/or the $M^+:Y$ ratio may be 0.01 to 2 and/or the R:Y ratio may be 0.01 to 2.

The method of the invention requires the reaction mixture to contain sufficient water to permit extrusion of the reaction mixture. The reactor may contain a further amount of water such that under the applied vapor phase conditions that water is made available to the crystallizing extrudate.

Preferably the preformed extrudate includes seed crystals of the molecular sieve, to facilitate the crystallization reaction. The seeds may be present in a wide range of concentration eg from 0.1 to 40 wt % of the extrudate, such as from 0.2 to 5 wt %.

In one embodiment of the invention, the preformed extrudate mixture may be exposed to an autogenous pressure and temperature which allow crystallization of the mixture under vapor phase conditions. Suitable pressures may be in the range, for example, of from 345 kPag (50 psig) to 6.9 MPag (1000 psig), preferably from 550 kPag (80 psig) to 3.95 MPag (500 psig), and more preferably 690 kPag (100 psig) to 2.07 MPag (300 psig). Suitable temperatures may vary from 50° C. to 500° C., preferably from 80° C. to 250° C., more preferably from 100° C. to 250° C. The reactor may comprise an autoclave or any other suitable chamber in which controlled pressure and elevated temperature conditions for promoting crystallization can be provided.

In another preferred embodiment of the invention, the pre-extruded mixture is provided within the reactor on a support, the support being adapted to allow removal of the excess alkali metal hydroxide eg caustic solution during crystallization. The support spaces the extrudate from the reactor wall. The support may also promote heat circulation during crystallization of the synthesized mixture. As the support enables removal of the excess alkali metal hydroxide eg caustic during crystallization, a critical level of alkali metal hydroxide eg caustic in the extruded mixture is maintained uniformly which will result in the formation of good quality zeolite in-situ extrudate. The support may comprise one or more apertures to facilitate separation of leached alkali metal hydroxide eg caustic from the extrudate. The apertures also promote heat exchange between the extrudate and the reactor.

To date, it has been known that molecular sieves may be prepared by a method called the in-situ extrudate technique. This process involves formation of an extrudate followed by crystallization in an autoclave. We have discovered that in the prior art preparation technique, leached caustic solution from the pre-formed extrudate reacts with portions of the extrudate which are in contact with the caustic solution. This results in a poor, non-uniform product having poor mechanical properties and in particular having a low crush strength in comparison to zeolites which are synthesized via conventional hydrothermal treatments. In the present invention, the method provides for separation of the pre-formed extrudate from the excess alkali metal hydroxide solution or excess caustic, for example by bearing the pre-formed extrudate on a support in the reactor, which results in a higher quality crystalline extrudate product, thereby overcoming a longstanding problem in molecular sieve (zeolite) catalyst crystals which are produced by means of conventional vapor phase crystallization processes.

In addition, removal of the alkali metal hydroxide caustic material during crystallization in turn enhances the vaporized atmosphere which further promotes the vapor phase crystallization. The support thus improves the vapor phase conditions and prevents the crystalline structure from being compromised by the inadvertent presence of unnecessary caustic within the formed crystalline structure during crystallization.

In a preferred embodiment, the pre-extruded synthesis mixture is spaced from at least one inner perimeter of the reactor by any suitable means such as the support. The mixture may be spaced from one or more walls. The mixture may also be spaced from a floor of the reactor. Separation of the mixture from the reactor walls promotes removal of the caustic agent and enhances heat circulation and promotes exposure of the mixture to the vapor phase.

The support may be formed by a sieve or grid or mesh. In this way the support does not affect the heat circulation whilst allowing efficient removal of the alkali metal hydroxide caustic agent during crystallization.

In another embodiment of the invention, the method is suited to crystallize extrudates of molecular sieve materials such as ZSM-5, ZSM-11, ZSM-12, ZSM-35, ZSM-48, Y and in particular, MCM-22 family molecular sieves. The MCM-22 family sieves may comprise MCM-22, MCM-49 and MCM-56.

In a further embodiment, the pre-formed extrudate additionally comprises an already synthesized further molecular sieve to form a dual molecular sieve after crystallization. The synthesized further molecular sieve may comprise, for example, zeolite beta, zeolite Y, Mordenite, ZSM-5 or ZSM-12.

In a preferred embodiment of the invention, the tetravalent element is silicon and the source of ions thereof preferably comprises a source of silica. The trivalent element is preferably aluminum and the source of ions thereof preferably comprises a source of alumina. In a particular embodiment, there is thus provided a method of preparing a molecular sieve comprising:

In a further embodiment, combinations of extrudates of the MCM-22 family with an open network structure of interconnected crystals are prepared by crystallizing HMI-containing preformed extrudate reaction mixtures under vapor phase conditions. The mixtures may contain seed crystals for each of the MCM-22, MCM-49, and MCM-56.

In a preferred embodiment of the invention, the compositions of the pre-formed extrudate for making MCM-22 or MCM-49 or MCM-56 or mixtures thereof may comprise (molar ratios):

| | | |
|---|---|---|
| (v) | $SiO_2/Al_2O_3$: | 10-500; |
| (vi) | $OH^-/SiO_2$: | 0.001-0.5; |
| (vii) | $Na/SiO_2$: | 0.001-0.5; |
| (viii) | $HMI/SiO_2$: | 0.05-0.5; |
| (ix) | $H_2O/SiO_2$: | 1-20; and, |

In the case where seed crystals are present, the seed concentration of the respective MCM-22, MCM-49 or MCM-56 seed crystals is preferably 0.1 to 40 weight % of the extrudate.

Dual zeolite crystals such as Beta/MCM-22 may be synthesized in a similar fashion. The reaction mixture may comprise silica, alumina, caustic, water, Beta and MCM-22 seed crystals and a structure directing agent. The resulting dual zeolite extrudates comprise a high surface area, high porosity, high crush strength, high activity and intergrown crystal morphology.

In another embodiment of the invention, the pre-extruded mixture comprises two or more phases of zeolite. In this way, dual zeolite or multiple zeolite catalyst systems can be produced.

In a further embodiment of the invention there is provided a method for preparing a catalyst comprising preparing a molecular sieve according to the method as hereinbefore described and activating the sieve to form the catalyst. The sieve may be activated for example by water post-treatment of the crystal and/or by surface modification. Suitable surface modification may comprise surface treatment to provide a metal oxide on the catalyst surface such as aluminum oxide.

In yet another embodiment of the invention, there is provided a catalyst which is formed from a zeolite crystal produced by means of the afore described method.

In a further embodiment of the invention, there is provided a catalyst formed from a pre-extruded mixture, said mixture being crystallized under vapor phase conditions whereby excess caustic agent is removed to form a catalyst with low density, high intrusion volume and high crush strength. The catalyst of the invention may also be suitable as a catalyst additive to enhance the performance of existing catalysts.

By virtue of the manufacturing method as herein described, the molecular sieves produced and the corresponding catalyst may for example comprise a surface area of at least 300 $m^2/g$ preferably at least 500 $m^2/g$ and more preferably at least 600 $m^2/g$, as measured by BET surface area analysis using a Tristar 3000 instrument available from Micromeritics Corporation of Norcoss, Ga., USA.

The crush strength values as reported herein are measured according to the Mobil Test using an anvil/strike plate instrument by determining the resistance of formed molecular sieve extrudate to compressive force. The measurement is performed on cylindrical extrudate having a length to diameter ratio of at least 1:1 and a length greater than ⅛" (0.32 cm). The determination is performed by placing the extrudate sample between the driven anvil and the fixed strike plate of an instrument comprising a Willrich Test Stand in combination with an Ametek Electronic Force Guage. The Test Stand comprises a movement that holds the Force Guage, and a strike plate. The strike plate is considerably larger than the anvil, and during testing carries the extrudate pellet under test. The anvil portion of the instrument comprises a rectangular ⅛"×½" (0.32 cm×1.27 cm) anvil surface arranged to apply compressive force to the pellet carried on the strike plate during the testing procedure. Prior to performing the test the minimum gap between opposed surfaces of the anvil and strike plate is about half the diameter of the cylindrical extrudate pellet.

The sample is prepared by placing the extrudate pellet in a crucible and drying at 121° C. (250° F.) for at least 1 hour. This step may be eliminated if the sample has been previously dried or calcined. Thereafter, the crucible containing the sample is placed on a crucible tray which is transferred to a muffle furnace at 538° C. (1000° F.) for 1 hour. Drying temperature/time may be altered as appropriate for the material under evaluation. However, consistency in treatment and drying between samples is imperative. All samples being compared for a given project or family should be evaluated after pretreatment at the same temperature/time. After such heating the crucible is removed from the furnace and sealed in a desiccator until cool.

For crush strength determination of a particular molecular sieve product, a representative sample of typically 25 cylindrical extrudate pellets is tested. Such pellets, once cooled in the desiccator, are placed in a buchner funnel under nitrogen flow. For testing a pellet is removed from the funnel using tweezers and placed on the strike plate directly under the raised anvil in a configuration such that the longitudinal axis of the cylindrical pellet is at 90° to the longitudinal axis of the ⅛"×½" (0.32 cm×1.27 cm) anvil shoe; with the pellet extending entirely across the ⅛" (0.32 cm) width of the anvil shoe. In this configuration, when under test, the anvil subjects a ⅛" (0.32 cm) longitudinal portion of the cylinder wall to the applied compression force. Once the pellet is in the required configuration, the instrument is activated such that the anvil is lowered in controlled fashion to apply gradually increasing force to a 1/8" (0.32 cm) contact area along the "spine" of the pellet until the pellet is crushed. The force reading displayed on the instrument guage at the point of collapse of the pellet is recorded. This technique is repeated for the 25 pellets of the sample, and the average measured crush strength value for the molecular sieve over the 25 readings is calculated. This crush strength is reported in normalized fashion as the average applied force per unit length along the spine of the extrudate to which the anvil sole is applied. Since the anvil dimension is 1/8" (0.32 cm) the crush strength is reported as force units (lb, kg) per length unit (inch, cm). Thus, if the measured force is, say, 2 lbs (0.91 kg) over the 1/8" (0.32 cm) width of the anvil, the crush strength would be reported as 16 lb/inch (2.84 kg/cm). As mentioned, the important feature of this test method is the comparative crush strength values obtained for different molecular sieves.

Preferably the molecular sieve products of the method of the invention have crush strength measured by the above-described Mobil Test of at least 5.4 kg/cm (30 lb/inch), more preferably at least 7.2 kg/cm (40 lb/inch) and most preferably at least 9.8 kg/cm (55 lb/inch).

According to another embodiment of the invention there is provided an organic compound eg (hydrocarbon) conversion process comprising contacting an organic eg hydrocarbon feedstock with a catalyst or catalyst additive as hereinbefore described under conversion conditions to convert the feedstock to converted product.

The catalyst compositions of present invention are useful as catalyst in a wide range of processes, including separation processes and hydrocarbon conversion processes. In a preferred embodiment, the catalyst composition of the present invention may be used in processes that co-produce phenol and ketones that proceed through benzene alkylation, followed by formation of the alkylbenzene hydroperoxide and cleavage of the alkylbenzene hydroperoxide into phenol and ketone. In such processes, the catalyst of the present invention is used in the first step, that is, benzene alkylation. Examples of such processes includes processes in which benzene and propylene are converted to phenol and acetone, benzene and C4 olefins are converted to phenol and methyl ethyl ketone, such as those described for example in international application PCT/EP2005/008557, benzene, propylene and C4 olefins are converted to phenol, acetone and methyl ethyl ketone, which, in this case can be followed by conversion of phenol and acetone to bis-phenol-A as described in international application PCT/EP2005/008554, benzene is converted to phenol and cyclohexanone, or benzene and ethylene are converted to phenol and methyl ethyl ketone, as described for example in PCT/EP2005/008551.

The catalyst composition of the present invention is useful in benzene alkylation reactions where selectivity to the monoalkylbenzene is required. Furthermore, the catalyst of the present invention is particularly useful to produce selectively sec-butylbenzene from benzene and C4 olefin feeds that are rich in linear butenes, as described in international application PCT/EP2005/008557. Preferably, this conversion is carried out by co-feeding benzene and the C4 olefin feed with the catalyst of the present invention, at a temperature of about 60° C. to about 260° C., for example of about 100° C. to 200° C., a pressure of 7000 kPa or less, and a feed weight hourly space velocity (WHSV) based on C4 alkylating agent of from about 0.1 to 50 hour-1 and a molar ratio of benzene to C4 alkylating agent from about 1 to about 50. The catalyst composition of the present invention is also useful catalyst for transalkylations, such as, for example, polyalkylbenzene transalkylations.

BRIEF DESCRIPTION OF THE DRAWINGS

Embodiments of the invention will now be described by way of example only and with reference to the accompanying drawings in which.

DETAILED DESCRIPTION OF THE INVENTION

In an embodiment of the invention to prepare a zeolite catalyst, a pre-formed mixture is prepared from the following compounds: silica, alumina, a caustic agent, water, seed crystals and a structure directing agent. Typically, the silica and alumina ratios define the type of zeolite crystal that can be produced. Various examples are described herein below but generally, the silica/alumina ratio is between 10 and infinite. The caustic agent is preferably sodium hydroxide although potassium ions can also be used. The structure directing agent is typically HMI for making in-situ extrudate with a structure type of MWW although other structure directing agents or templates may be used.

Figure 1:
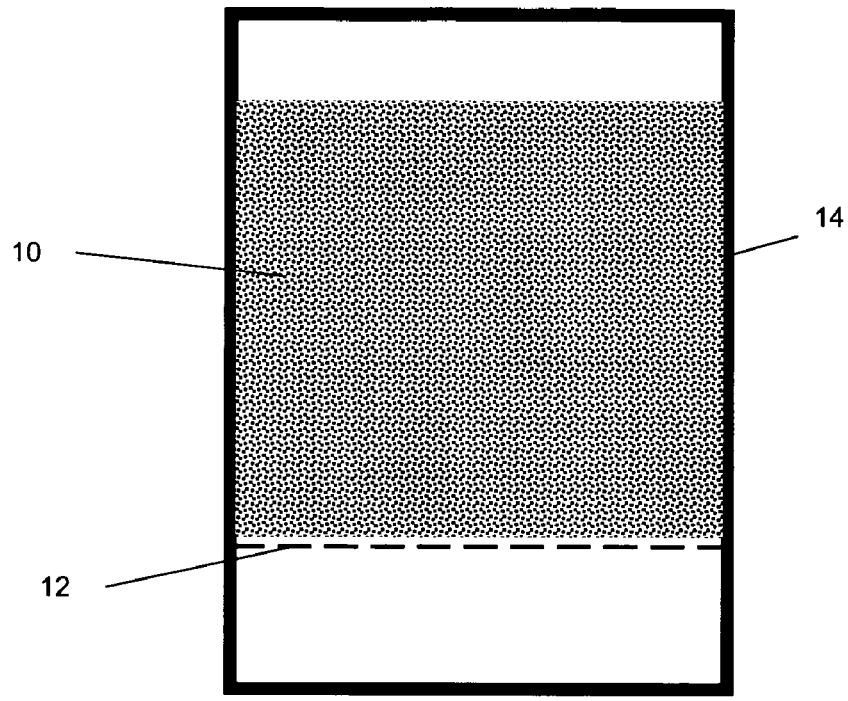
FIG. 1 presents a diagrammatic cross sectional view of a chamber for crystallizing a molecular sieve synthesis mixture under vapor phase conditions according to one embodiment of the invention.

Now turning to FIG. 1, the mixture is extruded by means of a conventional extruder such as a 5.08 cm (2 inch) Bonnot extruder and the extruded mixture (10) is provided on a support (12) for location inside an autoclave chamber (14). The pre-formed extruded mixture (10) is subsequently crystallized under vapor phase conditions to form the zeolite crystal catalyst whereby the excess caustic agent is removed from the crystallized material during crystallization. As the support (12) separates the mixture from the floor of the chamber, this promotes removal of the excess caustic agent and enhances heat circulation and promotes exposure of the mixture to the vapor phase.

Figure 2:
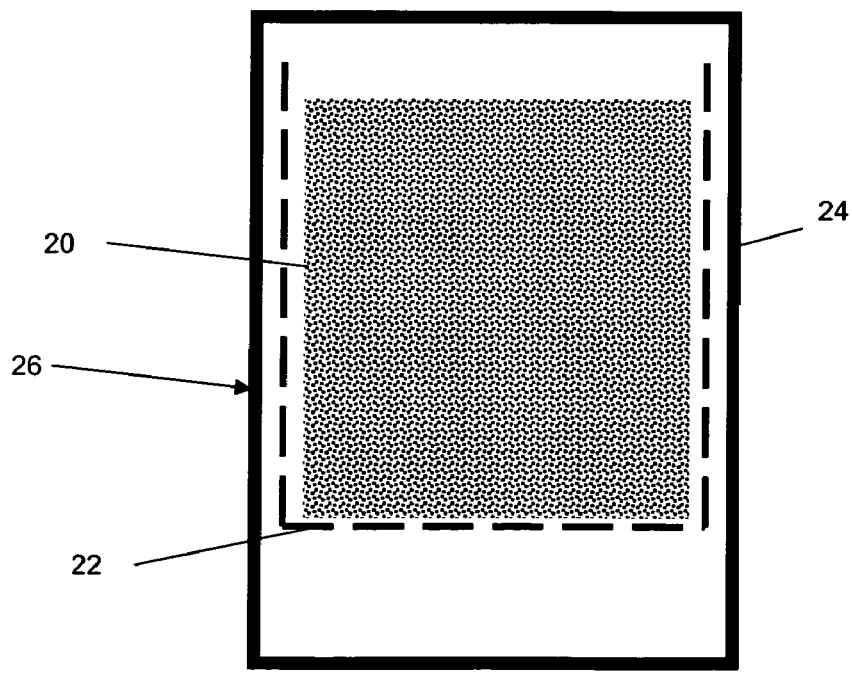
FIG. 2 presents a diagrammatic cross sectional view of a chamber for crystallizing a molecular sieve synthesis mixture under vapor phase conditions according to another embodiment of the invention.

In FIG. 2, the mixture (20) is located on a different support (22) which spaces the mixture from the perimeter or surrounding walls (26) of the autoclave chamber (24). This arrangement further enhances the removal of the caustic agent and enhances heat circulation and promotes exposure of the mixture to the vapor phase. This in turn increases the crush strength and the silica/alumina ratio as will be evident from the below Examples 1 and 2.

Embodiments of the invention will now be described in the following Examples to further illustrate the invention.

Preparation of MCM-22 Pre-formed Extrudate Mixture

Extrudates for MCM-22 vapor phase in-situ crystallization were prepared from a mixture of 908 g of Ultrasil Non-PM silica, 330 g of HMI, 180 g of sodium aluminate solution (45%), and 104 g of 50% sodium hydroxide solution, 950 g of de-ionised (DI) water, and 40 g of MCM-22 seed crystals. The mixture had the following molar composition:

| | | |
|---|---|---|
| (x) | $SiO_2/Al_2O_3 =$ | 29.4 |
| (xi) | $H_2O/SiO_2 =$ | 4.54 |

|        |                                    |      |
|--------|------------------------------------|------|
| (xii)  | OH⁻/SiO$_2$ =                      | 0.17 |
| (xiii) | Na⁺/SiO$_2$ =                      | 0.17 |
| (xiv)  | HMI/SiO$_2$ =                      | 0.23 |

The mixture was mulled and formed into a 0.16 cm (1/16") diameter cylinder extrudate using a 5.08 cm (2") Bonnot extruder. The extrudates were then stored in a sealed container before use in the below Examples 1 and 2.

Example 1

A 750 g sample of the above-formed wet pre-formed extrudate was placed in a 2-liter autoclave with wire mesh support as shown in FIG. 1. The mesh size of the support was 2 mm. The distance between bottom of autoclave and wire mesh support is >1.25 cm (½").

The extrudate was crystallized at 160° C. (320° F.) for 96 hrs. After the reaction the product was discharged, washed with water and dried at 120° C. (250° F.), the XRD pattern of the synthesized material showed the typical pure phase of MCM-22 topology. Scanning Electron Microscopy (SEM) analysis showed that the material is composed of agglomerates of platelet crystals (with a crystal size of about 1 microns). The synthesized extrudate was pre-calcined in nitrogen at 482° C. (900° F.) for 3 hrs and was then converted into the hydrogen form by three ion exchanges with ammonium nitrate solution at room temperature, followed by drying at 120° C. (250° F.) and calcination at 540° C. (1000° F.) for 6 hours. The resulting extrudate crystals have a SiO$_2$/Al$_2$O$_3$ molar ratio of 24.1, surface area of about 680 m2/g, crush strength of 11.3 kg/cm (63 lb/inch), particle density of 0.432 g/cc, bulk density of about 0.25 g/cc (ASTM D4284), intrusion volume of 1.72 ml/g (measured in accordance with ASTM D4284 Standard Test Method for Determining Pore Volume Distribution of Catalyst by Mercury Intrusion Porosimetry).

Example 2

A 500 g sample of the wet pre-formed extrudate produced as described in Example 1 was placed in a 2-liter autoclave with wire mesh holder as shown in FIG. 2. The mesh holder separates the sample from the bottom of autoclave and side walls by a distance of greater than 1.25 cm (½").

The extrudate was crystallized at 160° C. (320° F.) for 96 hrs. After the reaction the product was discharged, washed with water and dried at 120° C. (250° F.). The XRD pattern of the synthesized material again showed the typical pure phase of MCM-22 topology. The SEM showed that the material is composed of agglomerates of platelet crystals (with a crystal size of about 0.5 microns). The crush strength of the synthesized sample was measured at 12.35 kg/cm (69 lb/inch) which is higher than the crystal in Example 1. The extrudate was pre-calcined in nitrogen at 482° C. (900° F.) for 3 hrs and then was converted into the hydrogen form by three ion exchanges with ammonium nitrate solution at room temperature, followed by drying at 120° C. (250° F.) and calcination at 540° C. (1000° F.) for 6 hours. The resulting extrudate crystals have a SiO$_2$/Al$_2$O$_3$ molar ratio of 24.2.

Preparation of MCM-22 Pre-Formed HMI-Free Extrudate Mixture

Aluminosilicate pre-formed extrudates for MCM-22 vapor phase in-situ crystallization were prepared from a mixture of 908 g of Ultrasil Non-PM silica, 180 g of sodium aluminate solution (45%), and 104 g of 50% sodium hydroxide solution, 1080 g of DI water, and 40 g of MCM-22 seed crystals. The mixture had the following molar composition:

|         |                           |      |
|---------|---------------------------|------|
| (xv)    | SiO$_2$/Al$_2$O$_3$ =     | 29.4 |
| (xvi)   | H$_2$O/SiO$_2$ =          | 4.54 |
| (xvii)  | OH⁻/SiO$_2$ =             | 0.17 |
| (xviii) | Na⁺/SiO$_2$ =             | 0.17 |

No HMI was present in the mixture. The mixture was mulled and formed into a 0.16 cm (1/16") diameter cylinder extrudate using a 5.08 cm (2") Bonnot extruder. The extrudates were then stored in a sealed container before use. Dried extrudates were prepared separately by drying the wet extrudates in an oven at 120° C. (250° F.) for 2 hours. These extrudates were then used in below Examples 3 and 4

Example 3

The wet extrudates were placed in a 2-liter autoclave with wire mesh support as shown below. The distance between the bottom of the autoclave and the wire mesh support was greater than 1.25 cm (½"). A mixture of 300 g of DI water and 200 g of HMI was added to the bottom of the autoclave. The extrudates were crystallized at 160° C. (320° F.) for 120 hrs. After the reaction, the product was discharged, washed with water, and dried at 120° C. (250° F.). XRD patterns of the as-synthesized and calcined materials showed the typical pure phase of MCM-22 topology identical to the topology of the MCM-22 as prepared in the presence of HMI. SEMs of the as-synthesized material showed that the material was composed of agglomerates of platelet crystals with a crystal size of about 1-2 microns. The resulting dried extrudate had a SiO$_2$/Al$_2$O$_3$ molar ratio of 22.2 and crush strength of 3.6 kg/cm (20 lb/inch). Calcined extrudate had a surface area of 640 m$^2$/g, bulk density of 0.41 g/ml, and a total intrusion volume of 1.75 ml/g (measured in accordance with ASTM D4284 Standard Test Method for Determining Pore Volume Distribution of Catalyst by Mercury Intrusion Porosimetry).

Example 4

The dried extrudates were placed in a 2-liter autoclave with wire mesh support located near the bottom of the autoclave so that the distance between bottom of autoclave and wire mesh support is >1.25 cm (½"). A mixture of 200 g DI water and 200 g of HMI was added to the bottom of the autoclave. The extrudates were crystallized at 160° C. (320 F) for 132 hrs. After the reaction, the product was discharged, washed with water, and dried at 120° C. (250° F.). The XRD pattern of the as-synthesized material showed the typical pure phase of MCM-22 topology. The SEM of the as-synthesized material showed that the material was composed of agglomerates of platelet crystals (with an crystal size of about 1-2 microns). The resulting dried extrudate had a SiO$_2$/Al$_2$O$_3$ molar ratio of 25.4 and crush strength of 7.5 kg/cm (42 lb/inch). Calcined extrudate had a surface area of 540 m2/g, a bulk density (measured in accordance with ASTM D4284) of 0.6 g/ml, and a total intrusion volume (measured in accordance with ASTM D4284) of 1.07 ml/g.

Preparation of MCM-49 Pre-Formed Extrudate Mixture

Extrudates for MCM-49 vapor phase in-situ crystallization were prepared from a mixture of 908 g of Ultrasil Non-PM silica, 348 g of HMI, 262 g of sodium aluminate solution (45%), and 36 g of 50% sodium hydroxide solution, 576 g of DI water, and 40 g of MCM-49 seed crystals. The mixture had the following molar composition:

| | | |
|---|---|---|
| (xix) | $SiO_2/Al_2O_3 =$ | 20.8 |
| (xx) | $H_2O/SiO_2 =$ | 3.11 |
| (xxi) | $OH^-/SiO_2 =$ | 0.15 |
| (xxii) | $Na^+/SiO_2 =$ | 0.15 |
| (xxiii) | $HMI/SiO_2 =$ | 0.24 |

The mixture was mulled and formed into 0.16 cm (1/16") cylinder extrudates using a 5.08 cm (2") diameter Bonnot extruder. The extrudates were then stored in a sealed container before use in Examples 5 and 6.

Example 5

A 300 g sample of the above formed wet extrudate was loaded in a 600 ml autoclave without providing a support so that the mixture was in direct contact with the autoclave walls.

The extrudate was crystallized at 160° C. (320° F.) for 96 hrs. After the reaction the product was discharged, washed with water and dried at 120° C. (250° F.). A significant amount of clumps of extrudates or loose powder were found at the bottom of the autoclave. The XRD patterns of the synthesized MCM-49 material collected from the top showed a poor crystalline phase of MCM-49 topology, and clump materials collected from the bottom shows MCM-49 and impurity phase of ZSM-35. Continuing the crystallization for 24-48 hrs produced a product with more ZSM-35 impurity. The SEM of the "good quality" MCM-49 synthesized material showed that the material is composed of agglomerates of intergrown platelet crystals (with a crystal size of about 1 micron). The resulting extrudate crystals have a SiO2/Al2O3 molar ratio of 18.

Example 6

A 600 g sample of the pre-formed wet extrudate was placed in a 2-liter autoclave with wire mesh support as shown in FIG. 1. The distance between bottom of autoclave and wire mesh support is >1.25 cm (½"). 100 g of DI water was added to the bottom of the autoclave.

The extrudate was crystallized at 160° C. (320° F.) for 120 hrs. After the reaction the product was discharged, washed with water and dried at 120° C. (250° F.). Only small amount of clumps of the extrudate or loose powder was found at the bottom of the autoclave. The XRD pattern of the as-synthesized material showed the highly crystalline of MCM-49 topology. The SEM of the as-synthesized material shows that the material is composed of agglomerates of platelet crystals (with a crystal size of about 1 microns). The supported method appears to be an effective procedure for producing more homogenous and better quality product as compared to above Example 3. Crush strength of the dried extrudate was measured at 8.4 kg/cm (47 lb/inch). The as-synthesized extrudates were pre-calcined in nitrogen at 482° C. (900° F.) for 3 hrs and then were converted into the hydrogen form by three ion exchanges with ammonium nitrate solution at room temperature, followed by drying at 120° C. (250° F.) and calcination at 540° C. (1000° F.) for 6 hours. The resulting extrudate crystals have a SiO2/Al2O3 molar ratio of 17.2, surface area of approximately 620 m²/g.

Preparation of Beta/MCM-22 Pre-Formed Extrudate Mixture

Beta containing pre-formed extrudates were prepared from a mixture of 908 g of Ultrasil Non-PM silica, 500 g of beta crystal, 330 g of HMI, 180 g of sodium aluminate solution (45%), and 104 g of 50% sodium hydroxide solution, 1200 g of distilled water and 40 g of MCM-22 seed crystals. The mixture had the following molar composition:

| | | |
|---|---|---|
| (xxiv) | $SiO_2/Al_2O_3 =$ | 30.1 |
| (xxv) | $H_2O/SiO_2 =$ | 5.7 |
| (xxvi) | $OH^-/SiO_2 =$ | 0.17 |
| (xxvii) | $Na^+/SiO_2 =$ | 0.17 |
| (xxviii) | $HMI/SiO_2 =$ | 0.24 |
| (xxix) | Beta crystal/Ultrasil = | 35/65 (wt %) |

The mixture was mulled and formed into 0.127 cm (1/20") Quad extrudates using a 5.08 cm (2") Bonnot extruder. The extrudates were then stored in a sealed container before use in Example 7.

Example 7

The pre-formed wet extrudates were placed in a 2-liter autoclave with wire mesh support as shown below. The distance between bottom of autoclave and wire mesh support is greater than 1.25 cm (½").

The extrudates were crystallized at 150° C. (300° F.) for 96 hrs. After the reaction, the product was discharged, washed with water, and dried at 120° C. (250° F.). The XRD pattern of the as-synthesized material showed the typical mixed phases of MCM-22 and Beta. The scanning electro microscopy (SEM) of the as-synthesized material showed that the material was composed of agglomerates of MCM-22 platelet crystals (with a crystal size of 1-2 microns) and sphere-like Beta crystals. The SEM showed the cross-section of the resulting product. The as-synthesized extrudates were pre-calcined in nitrogen at 482° C. (900° F.) for 3 hrs and then were converted into the hydrogen form by three ion exchanges with ammonium nitrate solution at room temperature, followed by drying at 120° C. (250° F.) and calcination at 540° C. (1000° F.) for 6 hours.

The dried extrudate had a crush strength of approximately 14.3 kg/cm (80 lb/inch) and improved to 19.7 kg/cm (110 lb/inch) after calcination at 282° C. (540° F.). The calcined H-form extrudate crystals had a surface area of 715 m²/g, bulk density (measured in accordance with ASTM standard D4284) of 0.51 g/ml, and intrusion volume (measured in accordance with ASTM standard D4284) of 1.35 ml/g.

The above examples show that both the composition of the pre-formed extrudates and the reaction parameters, including the supporting method, are critical for producing a good quality and more homogeneous phase of products. The additions of HMI and seed crystals in the pre-formed extrudates accelerate the crystallization and promote the formation of the desired MCM-22/49 product, although these compounds can be omitted. The support grid functions to provide better heat circulation inside the reactor to allow separation of the excess caustic liquid from the mixture. This also prevents contamination of the mixture with accumulated caustic at the bottom of the autoclave. This in turn reduces clumps formation resulting from liquid phase reaction of the extrudates.

Evaluation in Cumene Test

Catalyst A: Water Wash Post-Treatment of MCM-22 of Example 1

A 5 g sample of MCM-22 of Example 1 was mixed with 13 ml of de-ionized water in a beaker. After soaking in water for about one hour, any excess water was drained and the catalyst was then air dried at room temperature until free flowing. It was further dried at 120° C. (250° F.) for about 16 hours. The modified sample was evaluated in an aromatics alkylation unit (Cumene unit) as will be discussed below.

Catalyst B: Surface Modification of Aluminum Oxide of MCM-22 of Example 1

A quantity of 0.695 g of aluminum nitrate nonahydrate was dissolved in about 14 ml of deionized water. This solution was dispersed evenly into 5 g of MCM-22 produced by conventional means without vapor phase crystallization. The wet mixture was then dried at 120° C. (250° F.) for about 16 hours and then calcined in air at 360° C. (680° F.) for 4 hours. Catalyst B has the same shape as catalyst A.

Catalyst C: Surface Modification of Aluminum Oxide of MCM-22 of Example 1

A quantity of 0.695 g of aluminum nitrate nonahydrate was dissolved in about 14 ml of deionized water. This solution was dispersed evenly into 5 g of MCM-22 produced conventionally without vapor phase crystallization. The wet extrudate was then dried at 120° C. (250° F.) for about 16 hours and then calcined in air at 360° C. (680° F.) for 4 hours.

Catalyst D: Activation of Beta/MCM-22 of Example 7

A 5 g sample of the catalyst of Example 7 was dried in an oven at 260° C. (500° F.) for 2 hours, prior to weighing into the catalyst basket.

Evaluation in Cumene Unit of Samples of Catalysts A, B, C and D.

Evaluation was carried out in a 300 ml autoclave reactor. 0.25 g of catalyst was transferred into the catalyst basket, and 6 gram of quartz chip was layer below and above the catalyst bed inside the basket. The catalyst and the basket were then dried in an oven at 260° C. (500° F.) for about 16 hours. This catalyst basket was then transferred into a 300 ml autoclave quickly with minimum exposure to ambient atmosphere. The catalyst was subsequently purged with dry nitrogen for 2 hours at 181° C. (358° F.) inside the reactor to remove air and moisture from the reactor. 156 g of benzene was transferred to the reactor under nitrogen and equilibrated with the catalyst for 1 hour at 130° C. (266° F.). 28 g of propylene was transferred into the reactor under 2.07 MPag (300 psig) of nitrogen pressure.

The reaction started as soon as propylene was added and a constant pressure of 2.07 MPag (300 psig) nitrogen blanketed the autoclave. The reaction was allowed to run for four hours and propylene was completely consumed during this period. Small samples of liquid were withdrawn from the autoclave at regular interval for analysis of propylene, benzene, cumene, diisopropylbenzene (DIPB), and triisopropylbenzene, using gas chromatography. Catalyst performance was assessed by a kinetic activity rate parameter which is based on the propylene and benzene conversion. For a discussion of the determination of the kinetic rate parameter, reference is directed to "Heterogeneous Reactions: Analysis, Examples, and Reactor Design, Vol. 2: Fluid-Fluid-Solid Reactions" by L K Doraiswamy and M M Sharma, John Wiley & Sons, N.Y. (1994) and to "Chemical Reaction Engineering" by O Levenspiel, Wiley Eastern Limited, New Delhi (1972). Cumene selectivity was calculated from the weight ratio of DIPB/cumene which was expressed as percentage.

The results of the evaluation of the catalysts of the invention A and D were compared with two different formulations of MCM-22 catalysts B, C as set out in the below table. The activity of the catalyst was normalized on the activity of Catalyst B.

TABLE 1

| Catalyst | Description | Normalized Activity % | Selectivity % DIPB/IPB* | Normalized % DIPB/IPB** |
|---|---|---|---|---|
| A | Example 1, in-situ MCM-22 extrudate, 0.16 cm cylinder | 166 | 20.3 | 120 |
| B | Conventional MCM-22 bound with alumina in 0.16 cm cylinder extrudate | 100 | 16.9 | 100 |
| C | Conventional MCM-22 bound with alumina in 0.127 cm quadrulobe extrudate | 171 | 20.8 | 123 |
| C | (repeated run) | 180 | 19.1 | 113 |
| D | Example 3, in-situ Beta/MCM-22 extrudate, 0.127 cm quadrulobe extrudate | 274 | 21.1 | 125 |

DIPB = diisopropylbenzene
IPB = isopropylbenzene
*Normalized to 1 gram cat load
**Normalized to Catalyst B performance It is known that for propylene alkylation of benzene, the reaction is diffusion limited, and extrudate with a high surface to volume ratio should normally have a higher activity. From the results, catalyst A, despite having a lower surface to volume ratio in comparison to catalyst C, has similar activity and selectivity (% DIPB/IPB). Also, in comparison to the conventionally produced MCM-22 catalyst B of the same extruded shape, catalyst A has much higher activity, and slightly higher % DIPB/IPB. The catalyst comprising a molecular sieve as produced by the method of the present invention shows dramatically higher activity than an alumina bound conventionally produced MCM-22 extrudate.

The unique properties of the resulting extrudates found from this invention include high surface area, high porosity, high crush strength, high activity, and an intergrown-crystal morphology. The H-form extrudate was tested in an aromatics alkylation unit and showed very encouraging performances for both activity and selectivity. The performance of the catalyst crystals can also be further enhanced by post treatments such as with water, mild acid solution washing, or metal oxide surface modification which are well known performance enhancing methods.

We claim:

1. A method of preparing a crystalline molecular sieve comprising:
   (a) providing a reaction mixture comprising at least one source of ions of tetravalent element Y, at least one source of alkali metal hydroxide, water, optionally at least one seed crystal, and optionally at least one source of ions of trivalent element X, said reaction mixture having the following mole composition:

| | |
|---|---|
| $Y:X_2 =$ | 10 to infinity |
| $OH^-:Y =$ | 0.001 to 2 |
| $M^+:Y =$ | 0.001 to 2 | wherein M is an alkali metal and the amount of water is at least sufficient to permit extrusion of said reaction mixture;

(b) extruding said reaction mixture to form a pre-formed extrudate; and (c) crystallizing said pre-formed extrudate under vapor phase conditions in a reactor to form said crystalline molecular sieve whereby excess alkali metal hydroxide is removed from the pre-formed extrudate during crystallization.

2. A method according to claim 1, characterized by the pre-formed extrudate comprising a structure directing agent R.

3. A method according to claim 1, characterized by the reactor containing water and/or structure directing agent R.

4. A method according to claim 3, characterized by the pre-formed extrudate being spaced from the water and/or structure directing agent in said reactor.

5. A method according to claim 1, characterized by the pre-formed extrudate being disposed in the reactor in a position that is spaced from at least one inner perimeter wall of said reactor.

6. A method according to claim 5, characterized by the reactor comprising a support for spacing the extruded mixture from the water and/or structure directing agent.

7. A method according to claim 1, characterized by the pre-formed extrudate being provided on a support in the reactor, the support being adapted to allow removal of the alkali metal hydroxide during crystallization of the pre-formed extrudate.

8. A method according to claim 1, characterized by the method comprising the additional steps of washing and drying the crystalline molecular sieve product.

9. A method according to claim 1, characterized by the mixture being dried prior to performing step b).

10. A method according to claim 1, characterized by the mixture being exposed to an autogenous pressure of 50 psig (345 kPa) to 500 psig (3450 kPa) and a temperature of 50° C. to 250° C. during crystallization.

11. A method according to claim 1, characterized by the $Y:X_2$ ratio being 50 to 5000.

12. A method according to claim 1, characterized by the $H_2O:Y$ ratio being 0.5 to 5.

13. A method according to claim 1, the $OH^-:Y$ ratio being 0.1 to 1.

14. A method according to claim 1, characterized by the $M^+:Y$ ratio being 0.01 to 2.

15. A method according to claim 1, characterized by the mixture being suited to form crystals of molecular sieves of the MCM-22 family under the applied vapor phase crystallization conditions.

16. A method according to claim 15, characterized by the MCM-22 family molecular sieves comprising MCM-22, MCM-49, and MCM-56.

17. A method according to claim 1, characterized by the pre-formed extrudate comprising a synthesized further molecular sieve to form a dual molecular sieve after crystallization.

18. A method according to claim 17, characterized by the synthesized further molecular sieve comprising zeolite beta, zeolite Y, Mordenite, ZSM-5 or ZSM-12.

19. A method according to claim 1, characterized by the pre-formed extrudate being free from a binder.

20. A method according to claim 1, characterized by the source of alkali metal hydroxide comprising a caustic agent.

21. A method according to claim 20, characterized by the caustic agent comprising sodium hydroxide solution.

22. A method according to claim 1, characterized by the tetravalent element comprising silicon.

23. A method according to claim 1, characterized by the trivalent element comprising aluminum.

24. A method according to claim 1 comprising water treating the crystallized extrudate and/or modifying the surface of the crystal to provide a metal oxide on the surface.

* * * * *